(12) United States Patent
Bunsick

(10) Patent No.: US 11,331,431 B2
(45) Date of Patent: May 17, 2022

(54) SYRINGE FOR INJECTING MEDICATION WITH OPENABLE AND CLOSABLE STOPPER

(71) Applicant: Gemini Medical, Inc., Shrewsbury, MA (US)

(72) Inventor: Philip Bunsick, Shrewsbury, MA (US)

(73) Assignee: Gemini Medical, Inc., Shrewsbury, MA (US)

( * ) Notice: Subject to any disclaimer, the term of this patent is extended or adjusted under 35 U.S.C. 154(b) by 179 days.

(21) Appl. No.: 16/671,504

(22) Filed: Nov. 1, 2019

(65) Prior Publication Data
US 2020/0164148 A1 May 28, 2020

Related U.S. Application Data

(60) Provisional application No. 62/771,041, filed on Nov. 24, 2018.

(51) Int. Cl.
*A61M 5/31* (2006.01)
*A61M 5/32* (2006.01)

(52) U.S. Cl.
CPC ........ *A61M 5/3129* (2013.01); *A61M 5/3148* (2013.01); *A61M 5/3202* (2013.01); *A61M 2005/3132* (2013.01)

(58) Field of Classification Search
CPC ...... A61M 2005/3132; A61M 5/31596; A61M 2005/31598; A61M 5/284; A61M 5/2066; A61M 5/2448; A61M 5/31511; A61M 5/31515; A61M 2005/31518; A61M 5/31593; A61M 5/315; A61M 2005/3114; A61M 5/31; A61M 5/19; A61M 5/178
See application file for complete search history.

(56) References Cited

U.S. PATENT DOCUMENTS

| | | | |
|---|---|---|---|
| 4,320,770 | A | 3/1982 | Etherington et al. |
| 5,876,372 | A | 3/1999 | Grabenkort et al. |
| 7,048,720 | B1 | 5/2006 | Thome, Jr. et al. |

(Continued)

FOREIGN PATENT DOCUMENTS

| | | | | |
|---|---|---|---|---|
| CN | 104645458 A | * | 5/2015 | ........ A61M 5/31596 |
| GB | 1529186 | | 10/1978 | |
| WO | WO 0147584 A1 | * | 7/2001 | ........ A61M 5/31511 |

OTHER PUBLICATIONS

International Search Report Written Opinion dated Jan. 22, 2020 for International Application No. PCT/US19/60385 filed Nov. 8, 2019.

*Primary Examiner* — Kami A Bosworth
*Assistant Examiner* — Emily J Becker
(74) *Attorney, Agent, or Firm* — Neil D. Gershon

(57) ABSTRACT

A syringe assembly having a barrel for storing a medication and a stopper positioned within the barrel and having an opening, the stopper separating the proximal and distal sections of the barrel. A plunger is movable axially within the barrel. A cover extends radially from the plunger, the cover movable within the barrel from an open position to a closed position, wherein in the open position the cover exposes the opening in the stopper to enable the medication to flow within the barrel from the proximal section to the distal section and in the closed position the cover covers the opening to prevent the flow of medication from the proximal to the distal section.

18 Claims, 21 Drawing Sheets

(56) References Cited

U.S. PATENT DOCUMENTS

| | | | |
|---|---|---|---|
| 9,463,284 B2* | 10/2016 | Raab et al. | A61M 5/31551 |
| 10,543,315 B2 | 1/2020 | Kalofolias | |
| 10,653,837 B2 | 5/2020 | Larsen | |
| 2013/0253464 A1 | 9/2013 | Jakob et al. | |
| 2018/0001032 A1* | 1/2018 | Kleyman et al. | A61M 2005/3126 |

* cited by examiner

SYRINGE FOR INJECTING MEDICATION WITH OPENABLE AND CLOSABLE STOPPER

This application claims priority from provisional application Ser. No. 62/771,041, filed Nov. 24, 2018, the entire contents of which are incorporated herein by reference.

BACKGROUND

Field of the Invention

This application relates to syringes for injecting medications and more particularly to pre-filled syringes for injecting select doses of medication.

Description of Related Art

Syringe assemblies, including syringes with hypodermic needles, and particularly disposable insulin syringes, are well known in the medical field and with diabetes patients requiring insulin injections in particular. A conventional insulin syringe typically includes a syringe barrel with an opening at the distal end that has a hypodermic needle and a plunger mechanism extending through the proximal end. The plunger mechanism typically includes a plunger rod extending through the barrel of the syringe and exiting through the proximal end of the barrel with the proximal end of the barrel being open to allow the plunger rod to exit to be able to draw in insulin or other medication and to inject. The plunger rod has a configured tip that is attached to a distal rubber syringe tip/stopper where the syringe tip/stopper provides a seal within the barrel to draw and inject insulin or other medications. With traditional insulin syringes, the plunger rod has a diameter similar or equal to the diameter of the inside of the syringe barrel. Insulin syringes, and syringes with a hypodermic needle, also have a protective needle cap placed over the needle to protect the needle and patient or healthcare professional from needle stick injuries.

In use, the protective needle cap is removed from the syringe to expose the needle. The plunger rod is then retracted through the syringe barrel to draw and then inject air into the vial of insulin and then retracted to fill the syringe with the insulin from the insulin vial, with the plunger rod extending out of the proximal portion of the syringe barrel and with the syringe barrel now full with the appropriate dose of insulin. For injection, the needle is inserted into the injection site by the patient or healthcare professional, and then the plunger rod is depressed so the rubber syringe tip/stopper and plunger rod force the insulin through the barrel to inject the insulin through the needle and into the patient. The insulin syringe needle is then withdrawn from the patient and the protective needle cap is placed back over the needle of the disposable syringe or the replacement needle and discarded as per protocol.

One drawback with current insulin syringes is that the user must draw insulin from the insulin vial for every insulin injection required. This means that the vial of insulin must be with, or very near, the patient at all times for convenient injections. Also, the user needs to draw the insulin multiple times throughout the day to draw insulin into the syringe for every injection. Not only is this inconvenient for the user, but it is also not discreet and it repeatedly exposes the needle which increases the chance of needle stick injuries. Since diabetic patients requiring insulin typically need to inject insulin anywhere from 3-10+ times per day, this multiple drawing of insulin adds significantly to the burden of the disease for the patient and discourages adherence to an appropriate insulin injection schedule or protocol.

Another drawback of prefilled syringes that are used in the healthcare field is the exposure of the extended plunger rod outside the syringe. With conventional syringes, prefilled syringes are not able to have the plunger rod within the syringe body, so prefilled syringes are typically stored and shipped with the plunger rod fully withdrawn and exposed (in the "ready to inject" position) or with the plunger rod separated from the syringe body, thereby requiring additional storage space and also requiring that the tip of the syringe be capped or sealed to ensure the medication in the prefilled syringe does not leak. Also, with current single-barrel prefilled syringes, the syringe can only be prefilled with one drug or medication which may not be optimal for patients or medications requiring a mixture or combination of two drugs.

Given the limitations of today's insulin syringe technologies, and prefilled syringes, and syringe technology in general, there is a need for a technology that enables the syringe to be filled once for use throughout the day and also a syringe that can be prefilled and easily carried, stored, or shipped.

SUMMARY OF THE INVENTION

The present invention overcomes the problems and deficiencies of the prior art. The devices of the present invention advantageously enable the syringe to be filled once for use throughout the day or for a single dose injection. The devices of the present invention further provide a syringe that can be prefilled and easily carried, shipped or stored without having the plunger rod extended and the medication ejection port capped, which takes up unnecessary carrying, storage and shipping space, adding to shipping costs and complexity of current prefilled syringes.

The syringes of the present invention advantageously enable the user to fill the syringe for a full or partial days use and to then easily draw and inject the amount of medication, such as insulin, required throughout the day. Additionally, the devices of the present invention overcome the problems and limitations of current prefilled syringes by enabling prefilled syringes to be filled with medication e.g., insulin, and then stored and shipped without leakage and with the plunger rod depressed. The syringes can be filled with medication, e.g., insulin, for daily use by the patient while enabling the syringe plunger to be set in the depressed position, as if it had already dispensed the medication, after it is filled. The ability to keep the plunger rod depressed while the syringe is full, or partially full, enables the syringe to be carried by a patient throughout the day for self-medication without the plunger rod being extended. This reduces the need for multiple draws of insulin from the insulin vial and eliminates the need for a patient to carry the insulin or medication vial throughout the day. Therefore, the medication vial does not need to be with the patient, the amount of time the needle is exposed is reduced, and a number of steps required for injection are eliminated which improves convenience and discretion/discreetness for injections and will also reduce the risk of needle stick injuries since the needle is exposed and manipulated for significantly less time.

In some embodiments, the syringes of the present invention can be filled with two medications and with the plunger rod partially depressed. In these embodiments, the stopper attached to the plunger rod can act as a barrier in the syringe between the two medications, and the two medications can be mixed when desired by the user.

The devices of the present invention can be used for insulin syringes for injecting insulin. However, the devices of the present invention are not limited to such insulin syringes and can additionally or alternatively be used for injection of other medication (other medication delivery syringes). In some embodiments, the devices are disposable syringes; in other embodiments, the devices are reusable syringes.

In accordance with one aspect of the present invention, a syringe assembly is provided comprising a barrel for storing a medication, a stopper positioned within the barrel and having an opening, the stopper separating proximal and distal sections of the barrel. A plunger is movable axially within the barrel and a cover extends radially from the plunger. The cover is movable with respect to the barrel from an open position to a closed position, wherein in the open position the cover exposes the opening in the stopper to enable the medication to flow within the barrel from the proximal to the distal section and in the closed position the cover covers the opening to prevent the flow of medication from the proximal section to the distal section in the barrel.

In some embodiments, the plunger is rotatable to move the cover between the open and closed positions. In some embodiments, the stopper is attached to the plunger and moves axially with axial movement of the plunger. The stopper can include a body portion having a dimension greater than a dimension of the cover so the cover can freely rotate within the body portion of the stopper.

In some embodiments, the cover has an open area movable into alignment with the opening of the stopper to allow the flow of medication; in other embodiments the cover has an opening therethrough movable into alignment with the opening of the stopper to allow the flow of medication through the openings. A proximal and/or distal seal can be positioned on the plunger rod.

In some embodiments, a first and second set of markings on an outer wall of the barrel to indicate a dose of fluid to be injected from the barrel is provided, the first set of markings containing numerals facing proximally and the second set of marking containing numerals facing distally.

In some embodiments, the plunger includes a cap having an indicator to indicate alignment of an opening area or an opening in the cover with the opening in the stopper.

In some embodiments, a second medication is positioned in the distal section of the barrel, and the cover is movable to an open position to mix the second medication with the medication from the proximal section.

In some embodiments, the plunger is depressable to inject the medication from the barrel and the plunger is stored in a depressed position.

In accordance with another aspect of the present invention, a syringe assembly is provided comprising a barrel for storing a medication, the barrel having a proximal section and a distal section. A stopper is positioned within the barrel and has an opening, the stopper separating proximal and distal sections of the barrel. The stopper is movable axially within the barrel and has an opening, the opening selectively closable and openable to allow flow of medication from the proximal section to the distal section to provide a selected dose of medication in the distal section of the barrel. A plunger is movable axially distally within the barrel to inject the medication which flowed into the distal section of the barrel from the proximal section.

In some embodiments, the syringe assembly includes a cover extending from the plunger, the plunger rotatable to move the cover from a first position covering the opening to a second position spaced from the opening to enable flow of medication through the opening.

In some embodiments, the plunger is depressable to inject the medication from the barrel and the plunger is stored in a depressed position.

In accordance with another aspect of the present invention, method of injecting medication from a pre-filled syringe is provided, the method comprising the steps of:
a) providing a syringe having a barrel, a stopper positioned within the barrel and a plunger movable axially within the barrel and rotatable with respect to the barrel;
b) rotating the plunger rod to move a cover of the plunger to an open position to open an opening in the stopper;
c) retracting the plunger proximally to move the stopper proximally to enable flow of a selected dose of medication distal of the stopper;
d) after step (c) rotating the plunger rod to move the cover to a closed position to close the opening in the stopper;
e) depressing the plunger to inject the medication distal of the stopper.

In some embodiments, after depressing the plunger, the method includes the steps of removing the syringe from the patient and storing the remaining medication within the syringe with the plunger in a position distal of a proximal position.

In some embodiments, the method further comprises the step of applying a second (or more) dose(s) of medication from the syringe, each dose including the steps of:
a) rotating the plunger rod to move the cover of the plunger to the open position to open the opening in the stopper;
b) retracting the plunger proximally to move the stopper proximally to enable flow of a second selected dose of medication distal of the stopper;
c) after step (b) rotating the plunger rod to move the cover to the closed position to close the opening in the stopper; and
d) depressing the plunger to inject the second dose of medication distal of the stopper.

In some embodiments, the step of opening the stopper mixes a first medication within the barrel proximal of the stopper and a second medication within the barrel distal of the stopper.

The method may further comprise the step of removing a protective cap from a needle of the syringe.

BRIEF DESCRIPTION OF THE DRAWINGS

Preferred embodiment(s) of the present disclosure are described herein with reference to the drawings wherein.

DETAILED DESCRIPTION OF PREFERRED EMBODIMENTS

Figure 1:
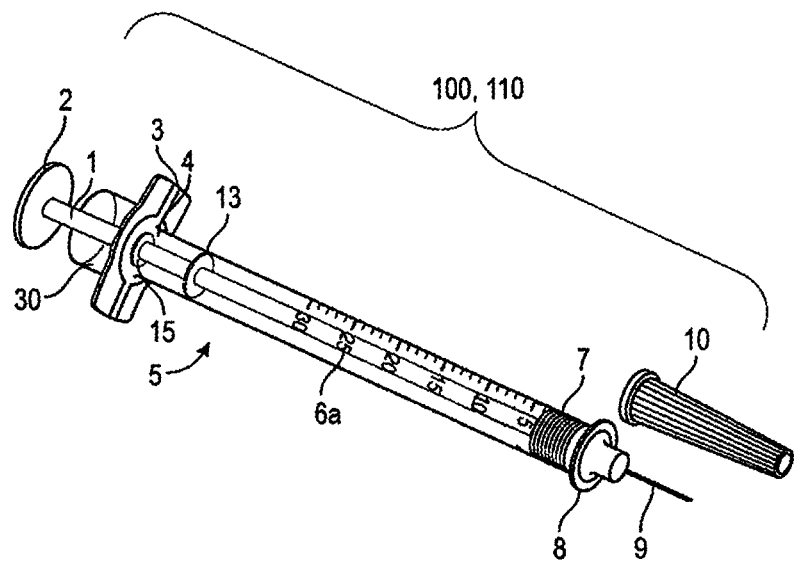
FIG. 1 is a perspective view of the insulin syringe assembly of one embodiment of the present invention having a needle.
Figure 2:
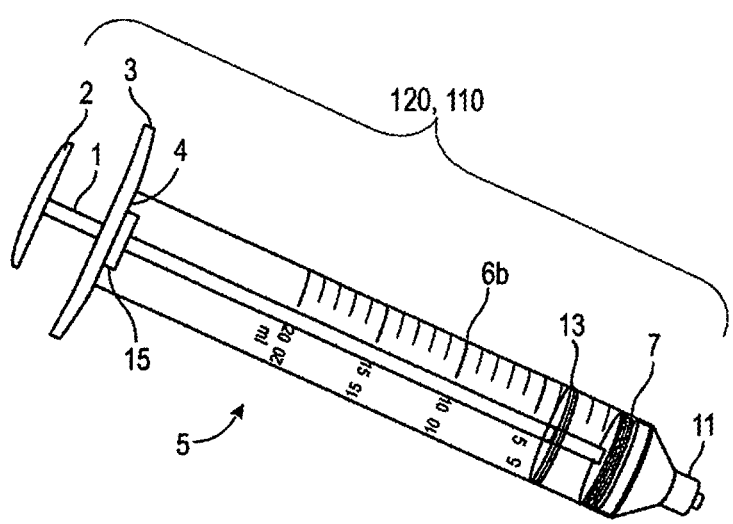
FIG. 2 is a perspective view of the syringe assembly of an alternate embodiment of the present invention without the needle and with a fixed luer lock at the ejection port.

Referring now to the drawings and particular embodiments of the present invention wherein like reference numerals identify similar structural features of the devices disclosed herein, FIGS. 1 and 2 illustrate two embodiments of the syringe of the present invention wherein FIG. 1 shows the disposable syringe (e.g., an insulin syringe) with an attached needle and FIG. 2 shows a disposable syringe (e.g., an insulin syringe) without an attached needle and shows the medication ejection port with a fixed luer lock system. The disposable syringe of FIG. 1 is designated generally by reference numeral 100 and the disposable of FIG. 2 is designated generally by reference numeral 120. Syringes 100 and 120 also differ in their external markings which are described below.

The systems/syringes of the present invention are described herein for storage and injection of insulin, however, it should be understood that the systems/syringes can be used for storage and injection of other medications.

Note as used herein, the term "distal" denotes components or regions further from the user and the term "proximal" denotes components or regions closer to the user.

The syringe assembly 100 and 120 in FIG. 1 and FIG. 2 includes a syringe barrel 5 for storing insulin (or other medications) for injection with dosage or storage volume markings 6a, 6b, respectively, along its length. The barrel 5 of syringe 100 has a distal tapered end with a needle housing hub 8 for housing a hypodermic needle or cannula 9 to inject medication. The needle 9 is protected between use by the protective needle cap 10 which sits over the needle to protect the user or healthcare professional from needle stick injuries and to protect the needle. The syringe assembly 120 does not have a needle, needle hub or housing unit but incorporates a syringe injection tip incorporating a fixed or rotatable luer locking system. The luer lock adjacent tip 11 of syringe 120 can connect the syringe to different pressure lines. The luer lock can also enable connection of various replaceable injection needles to the syringe. In some embodiments, the syringe does not incorporate a needle but has a distal housing hub or unit that allows replaceable needles to be attached to the distal syringe tip.

The syringes depicted in FIGS. 1 and 2 have a plunger rod system 110 which includes a plunger rod top/cap 2, a thin plunger rod 1, and a rotatable plunger rod door which is at the bottom or distal end of the plunger rod 1. Various plunger rod doors are shown in FIGS. 13A-13F and designated by reference numerals 22a-22f, respectively. The cap 2, plunger rod 1 and plunger rod door are either integrally formed or separate attached components so that rotation of the cap 2 rotates the rod door to open and closed the opening within the stopper as described in detail below.

The barrel 5 has a sealed proximal end 4. The thin elongated plunger rod 1 of the plunger rod system 110 is used to draw and inject insulin and allows space for insulin (or other medications) to be stored in the syringe barrel 5 when the plunger rod 1 is depressed. That is, it is dimensioned so its outer diameter is minimized to maximize the space between its outer dimeter and the inner diameter of the barrel 5. Finger flange 3 at a proximal region of the syringe 110 provide a "wings" configuration 18 (see FIG. 10), as it extends outwardly from a proximal end of the plunger rod 1. A rubber syringe tip/stopper 7 is positioned within a distal region of the barrel 5. Various embodiments of the rubber syringe tip for use with syringe 100 or syringe 120 are described below in conjunction with the discussion of FIGS. 15-24C. The stopper 7 separates the barrel 5 into a proximal section (region) 5a and a distal section (region) 5b and has an opening to allow flow of medication from the proximal section 5a into the distal section 5b and from the distal section 5b to the proximal section 5a when the plunger is depressed with the stopper hole open. The door of the plunger rod cooperates with the opening in the stopper 7 for opening and closing the opening as described in detail below. The stopper 7 acts a valve to allow or prevent medication flow between the proximal and distal sections. The stopper is also movable axially. Stated another way, the distal syringe tip/stopper and plunger rod act like a two way on-off stopcock or valve. When the syringe is on or open, the syringe tip/stopper attached to the plunger rod is able to move and set the plunger rod and syringe tip within the filled syringe barrel to a fully depressed position in a filled syringe and to the required dosing position needed to set the appropriate dose. When the distal syringe tip is closed, the syringe tip is completely sealed and is ready to inject.

The syringe barrel 5 has external markings 6a (FIG. 1) or 6b (FIG. 2) along its length to indicate to the user the dose to be injected and the amount of insulin or medication stored in the syringe barrel 5. The markings 6 on the syringe barrel 5 are placed in a manner such that it is easy for the user to visualize the dose on the syringe barrel 5. In alternate embodiments, the dose markings can be further apart making it easier to visualize and to set the dose.

In some embodiments of the present invention, two sets of dose and volume markings can be used with one set of markings in the upright position and another set of markings upside down (reversed) so the markings are easy to read when the syringe is pointed either up or down to aid in setting correct doses regardless of the direction the syringe is pointed. These different directions can be appreciated by the syringe of FIG. 2 having markings upside down (inverted with respect to the user) as well as markings facing upwardly. Such forward and reverse marking can also be provided on the syringe of FIG. 1 or on other syringes disclosed herein. Note the reverse orientation of the markings on the external walls of the barrel can be placed adjacent the opposite directed marking or on other regions of the circumference of the barrel, e.g., spaced 180 degrees apart.

Figure 3:
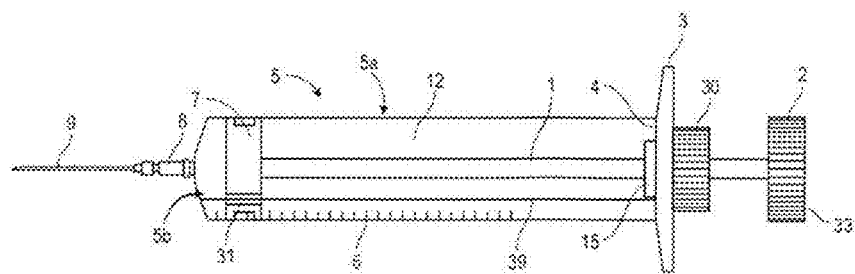
FIG. 3 is a side view of the insulin syringe assembly of FIG. 1 showing the thin plunger rod within the syringe barrel displaying the space provided for insulin or medication storage, the syringe rod shown in a depressed position.

The thin plunger rod 1 of FIG. 3 of the plunger rod system 110, has a diameter thinner, preferably much thinner, than the inner diameter of the syringe barrel 5 to allow the syringe to have adequate space or storage area 12 within the syringe barrel 5 to store the required amount of insulin or other medication for the user given the size of the syringe when the plunger rod is in the depressed (distal) position. This space is defined between the outer diameter of the plunger rod 1 and the inner diameter of the barrel 5. With the thinness of the plunger rod 1, the insulin syringe 100 maintains the functionality and performance of a syringe having a traditional plunger rod, with the added benefit of having insulin (or other medication) storage within the barrel. As an example, in one embodiment, the plunger rod is thin enough to allow the syringe barrel to store up to 50u or 100u of insulin while the plunger rod is in a depressed position. Other amounts/volumes are also contemplated. Note the plunger rod is sufficiently thin to maximize the amount of medication within the barrel of the syringe when the plunger rod is depressed while being strong enough to withstand multiple insulin or medication draws and injections without experiencing fatigue, bending, or breakage.

Figure 4:
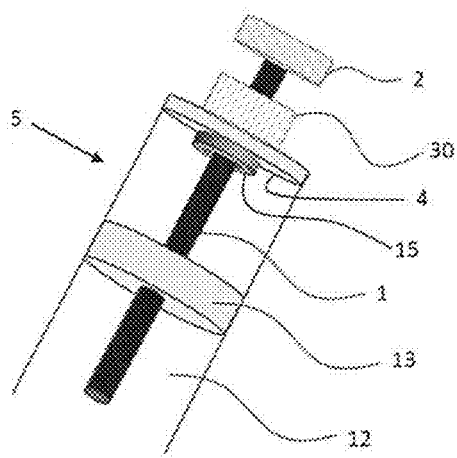
FIG. 4 is a perspective view of the syringe assembly of FIG. 1 showing the plunger rod within the syringe barrel in the depressed position.
Figure 5:
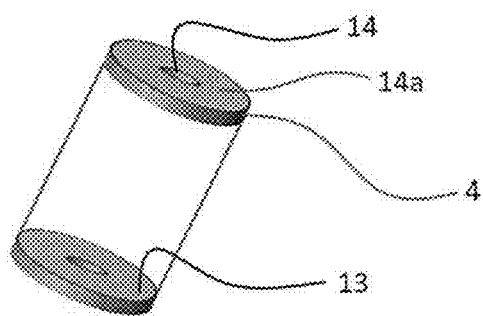
FIG. 5 is a perspective view of a region of the barrel of the syringe assembly of FIG. 1 showing the plunger rod exit port of the sealed proximal end of the syringe barrel and the inner rubber seal.

The sealed proximal end 4 of the proximal end of the syringe barrel 5 as shown in FIGS. 3-5 includes a plunger rod exit port 14, which is preferably centered within the syringe barrel 5 and where the plunger rod 1 extends through to extend outside (proximal of) the syringe barrel 5. The plunger rod 1 is moved axially in a plunging (pushing) and pulling motion to draw insulin into the syringe 100, inject insulin into the patient, and move the rubber syringe tip/stopper 7 attached thereto through the filled barrel 5. That is, once the barrel 5 of the syringe is filled, the plunger rod 1 is moved proximally with the stopper 7 in the open position to a select position by the user so a desired amount (units) of medication can flow from the proximal section to the distal section of the barrel 5. Once the desired volume of medication is in the distal section of the barrel, the stopper opening is closed and the plunger 1 is moved distally to inject the medication from the distal section of the barrel. As can be appreciated, in the initial position of the syringe, e.g., the storage position, the plunger rod is in the depressed (distal) position so the entire proximal section of the barrel 5 can be filled with medication. During use, select amounts of medication are moved from the proximal section of the barrel to the distal section, in accordance with the dosage desired, due to the interaction of the plunger rod door and stopper described below.

In some embodiments, the proximal seal 15 of the syringe barrel may be large enough to enable insulin or other medications to be injected directly into the syringe barrel 5 by a second syringe so the plunger and rubber syringe tip/stopper may remain in place while filling the syringe for use.

The proximal seal section at the plunger rod exit port 14 has a proximal seal 14a that ensures insulin does not leak from the syringe barrel while simultaneously ensuring, via its central opening, that the plunger rod 1 is centered and stable and that the plunger rod 1 is able to move freely in an axial direction within the barrel to draw and inject insulin and other medications.

The plunger rod exit port 14 may also enable air to enter the syringe barrel 5 to maintain stasis within the syringe barrel 5 when insulin is injected. The plunger rod exit port 14 in some embodiments is protected by a protective barrier 30, positioned proximal of the sealed proximal end 4 of the barrel 5 as shown in FIG. 4.

Adjacent the proximal seal section 14a of the syringe barrel 5 and the plunger rod exit port 14 is proximal rubber seal 15. The rubber seal component 15 of the sealed proximal end enables needles to be inserted through the rubber seal to allow insulin or other medication to be injected directly into the syringe barrel and behind the rubber syringe tip/stopper. The proximal rubber seal 15 is similar to an O-ring and prevents insulin leakage and allows the thin plunger rod 1 to move up and down (axially) more smoothly with reduced friction or stoppage of motion when it is engaged and is moved proximally to draw in insulin or other medications into the syringe barrel 5, when it is moved to set the dosing position, and when it is moved distally (depressed) to inject.

Figure 6A:
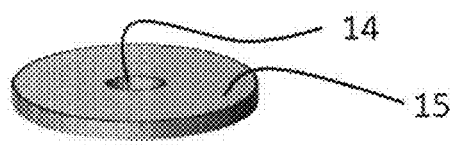
FIG. 6A is a perspective view of the rubber seal of FIG. 1 which is located on the plunger rod exit port and prevents leakage and allows the syringe barrel to move without friction or stoppage.
Figure 6B:
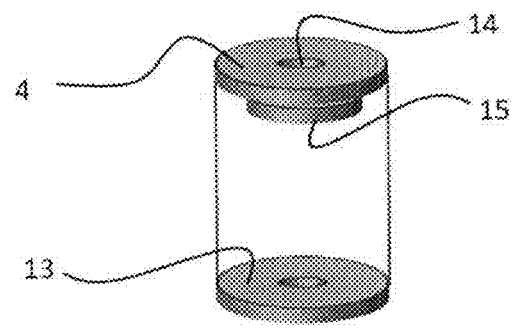
FIG. 6B is a perspective view of a region of the barrel of the syringe assembly of FIG. 1 showing one embodiment of the rubber seal.
Figure 6C:
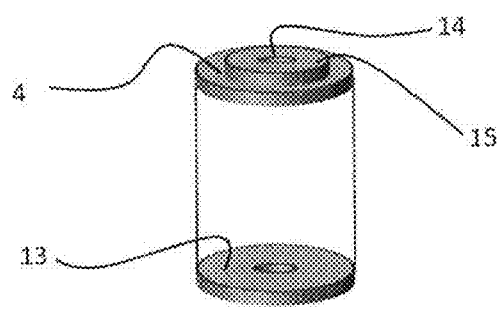
FIG. 6C is a perspective view of a region of the barrel of the syringe assembly showing an alternate embodiment of the rubber seal.

The seal 15 also enables a pre-filled syringe to be carried or transported since it prevents leakage from the barrel 5. The proximal rubber seal 15 is located within the syringe barrel 5 in the embodiment FIGS. 4 and 6B, distal of sealed proximal end 4; however, in alternate embodiments the proximal rubber seal can be positioned outside or external (proximal) to the syringe barrel 5 such as proximal seal 15a in the embodiment of FIG. 6C. In some embodiments, the rubber seal 15 enables other syringes (plungers), e.g., larger plungers, to inject insulin or other medications through this rubber seal so a plunger other than the plunger of the present invention can be used to fill the syringe. FIG. 7B illustrates another embodiment of the proximal rubber seal 15b, similar in function and configuration to seal 15 and 15a, except seal 15b is built into the sealed proximal end of the syringe, e.g., built into flange 3a. In some embodiments, it is large enough for a different syringe (plunger) to be used to inject insulin into the syringe barrel with the plunger rod depressed. The seal may also contain a lubricant to improve the plunger rod moving smoothly within the syringe barrel without friction which could cause plunger movement disruption or require excessive force to move the plunger rod. In certain embodiments, additional rubber seals may be used to ensure leakage is prevented.

An inner rubber seal 13 can be provided in some embodiments and is positioned within the barrel 5 distally of proximal rubber seal 15 to provide an additional seal between the plunger rod and syringe barrel walls to help prevent leakage of insulin and other medications from the syringe when it is filled. The distal seal 15 has an opening through which the plunger rod 1 extends. The inner rubber seal 13 can also provide positioning and additional stability support to the plunger rod 1. It further allows the plunger rod 1 and rubber syringe tip/stopper 7 to move easily and freely within the barrel 5. It further moves with the insulin and provides separation between the insulin and the air on the proximal side of the seal. The inner rubber seal can also provide a visual aid to the user to show the amount of insulin or medication remaining in the syringe. It is stable and able to easily move along the plunger rod without "tipping" or "sticking" to the plunger rod or syringe barrel to seal the medication within the syringe.

To be able to fully engage the disposable insulin syringe 100 of FIG. 1 or non-needle syringe 120 of FIG. 2, the plunger rod 1 is maneuvered by the user to open or close the hole or open area of the rubber syringe tip/stopper 7. To do this, the plunger rod top/cap 2 as shown in FIGS. 7A-12 (also referred to herein as the syringe cap) is rotated in a clockwise motion (to the right) to close the syringe tip/stopper hole and in a counterclockwise motion (to the left) to align the opening of the plunger rod door with the hole of the rubber syringe tip/stopper to open or expose the hole. Alternatively, it can be configured so that clockwise motion can open and counterclockwise motion can close the hole.

The plunger rod top/cap 2 in FIGS. 7A-12 preferably includes a body with sides that have an irregular surface, i.e., non-smooth surface to provide an additional grip to the user to be better able to rotate the plunger rod top/cap 2. More specifically, the syringe cap 2 can be rotated generally with the user's thumb and index fingers and the height of the cap from top to bottom (proximal to distal) is comfortable for the user to hold and rotate. The external grip lines or bevels that may be provided can extend from the top to the bottom of the cap 2 to help the user hold the cap 1 to rotate the plunger rod door (due to its connection via plunger rod 1) and avoid slippage and to help ensure a 1-1 torque response.

Figure 7A:
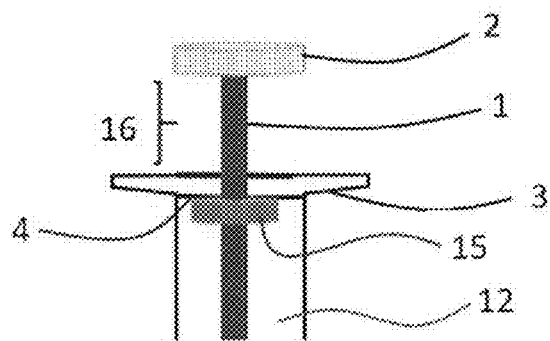
FIG. 7A is a side view of a proximal region of the syringe assembly of FIG. 1 showing the proximal seal and the plunger rod shown in the non-depressed position and the gap between the plunger rod cap and the proximal end of the syringe barrel.
Figure 7B:
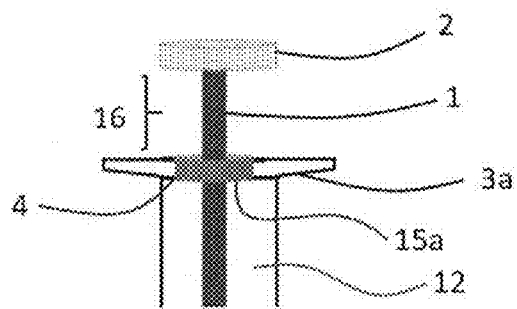
FIG. 7B is a view similar to FIG. 7A showing an alternate embodiment of the proximal seal located within the flange.
Figure 8A:
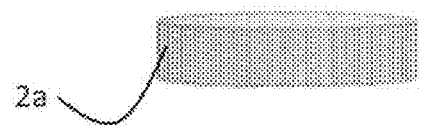
FIGS. 8A-8C are side views of three embodiments of the plunger rod top/cap.
Figure 8B:
Figure 8C:
Figure 9:
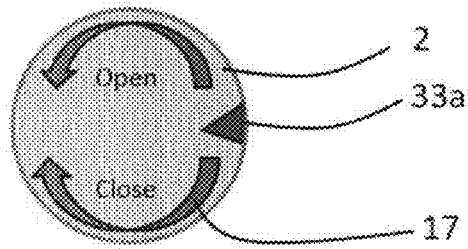
FIG. 9 is a top view of the plunger rod cap that includes markings indicating the direction to rotate the plunger rod door to open and close the hole of the rubber syringe tip/stopper.

FIGS. 7A and 7B also illustrates the gap 16 between the plunger rod cap 2 and the finger flange 3 or 3a when the plunger rod 1 is in the depressed position to be better able to draw in and to inject insulin and other medications and to maneuver the plunger rod 1 and syringe tip within the syringe barrel 5. FIGS. 8A-8C show differing cap heights (lengths from proximal to distal) of the plunger rod cap 2a, 2b, 2c, respectively, which can range from being very slim (short height) to looking more like a cap with a greater height. Other heights than those shown are also contemplated. Other irregular surfaces to enhanced gripping are also contemplated.

As seen in FIGS. 9, 10, 11, 12 the top or cap of the plunger rod 2 is shown from the top and displays the marking directions/instructions 17 for the user to know which direction to rotate the cap 2 (and connected plunger rod 1) to open or close the syringe tip hole. In this embodiment, to rotate the plunger rod door 22 to open the hole of the rubber syringe tip 7, the plunger rod cap 2 is rotated in a counterclockwise motion and is rotated to the left, and to close or cover the hole 25a, 25b, 25c, 25d, 25e, 25f (collectively hole 25) of the rubber syringe tip 7 (FIGS. 16-21) with the plunger rod door 22, and as outlined in FIGS. 9-12, the plunger rod cap 2 is rotated in a clockwise motion and is rotated to the right.

FIGS. 9-12 also illustrate markings 33a 33b, 33c, 33d (collectively marking 33) or alternatively a hole or open section on the cap 2 to indicate the location and alignment of the cap 2 with the opening of the plunger rod door at the distal end of the plunger rod 1. In certain embodiments the marking 33 or opening of the cap 2 may align with the foot of the plunger rod door. The markings can be of different shapes as shown to correspond to the shape of the door or opening in the tip/stopper 7.

When the plunger rod top/cap 2 is rotated to open or close the hole of the rubber syringe tip/stopper, the foot of the plunger rod door 22 moves to cover or close the hole (the closed position), or is moved so the plunger rod door 22 is moved away from the hole and the opening (or open section) on the plunger rod door is aligned with the hole of the rubber syringe tip/stopper so the hole is not covered and is fully open so insulin or medication can flow through the hole (the open position), enabling the plunger rod 1 and syringe tip/stopper to move through the insulin to set the appropriate position to deliver (inject) the required dose, or to be able to move to the fully depressed position so the syringe can be carried and transported with the plunger rod depressed.

In some embodiments, the syringe barrel can have a marking 39, as seen in FIG. 3 (and FIG. 27), that can be used to facilitate alignment of the door 21a-21f (collectively "door 21") of the plunger rod 1 of the plunger rod system and the open area 37a, 37b (collectively open area 37) or the opening 25a-25f (collectively opening 25) of the stopper 7. The marking 39 on the outer side wall of the syringe barrel 5 is aligned with the marking 31 for the open area 25 of the tip/stopper 7 and the open area or hole of the door 37 so that alignment of the marking 33 on plunger cap 2 with marking 39 helps guide opening and closing of the syringe tip/stopper as it indicates the position of the rotatable door. For example, alignment of marking 33 and marking 39 can indicate the door 22 is in the closed position to cover the opening 37. Thus, the marking confirms alignment with the hole of the syringe tip/stopper to the user as in these embodiments the rubber syringe tip/stopper has markings that indicate the approximate location of the hole to ensure alignment of the door or opening of the plunger rod system when it is rotated with the hole of the rubber syringe tip/stopper.

In summary, the rubber syringe tip/stopper has a shaped hole that is open to allow insulin or other medication to flow from one side of the rubber syringe tip/stopper to the other side, like a valve, when it is not covered or sealed, i.e., not closed/sealed by the plunger rod door. When the hole of the rubber syringe tip/stopper is covered (or closed) by the foot of the plunger rod door or other mechanical methods, the plunger rod is able to draw insulin or medication into the syringe barrel and to inject the measured amount of insulin or medication into the patient.

In alternate embodiments the rubber syringe tip/stopper itself can be maneuvered to create an opening, whereby the rubber syringe tip/stopper itself acts like a valve and can be independently opened and closed rather than being closed/sealed by a plunger rod door. Further, in some embodiments, the hole or opening of the rubber syringe tip/stopper has a thin rubber cover that allows for a seamless looking rubber tip/stopper top, but does not prevent insulin or other medications from flowing through the syringe tip/stopper when it is open and not covered.

Although the foregoing describes in detail a rotating mechanism to maneuver the plunger rod door between a closed position to cover the hole and an open position to open the hole of the rubber syringe tip, other mechanisms to maneuver the door of the plunger rod over and away from the hole are also contemplated to cover and open the syringe tip/stopper hole to provide opening and closing capabilities. These can include maneuvering mechanisms such as lifting, pivoting, sliding and tilting of the plunger rod door. In other embodiments, the rubber syringe tip/stopper itself could be able to function like a valve and could be rotated/maneuvered to provide opening and closing/sealing capabilities within the syringe barrel.

The finger flanges 3 referenced above are located on the proximal end of the syringe barrel 5. These finger flanges 3 aid the user in holding the syringe and maneuvering the plunger rod 1 to be able to draw in insulin and other medications into the syringe or to set the rubber syringe tip into an appropriate dosing position, and to aid in the injection.

Figure 10:
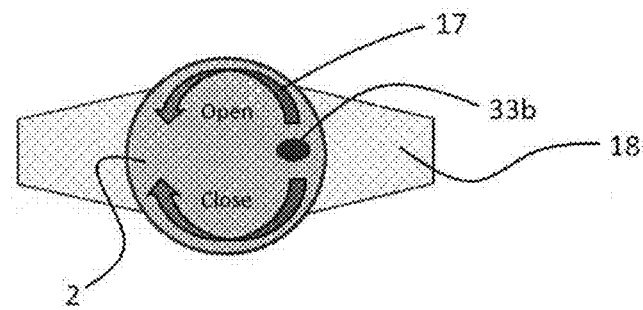
FIG. 10 is a top view of the plunger rod cap and proximal syringe barrel finger flange having a wing-shape configuration.
Figure 11:
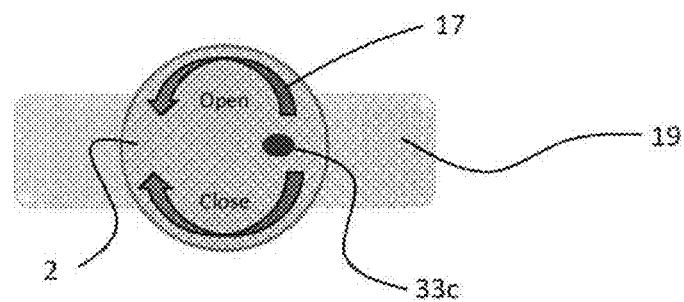
FIG. 11 is a top view of the plunger rod cap of FIG. 10 and an alternate embodiment of the proximal syringe barrel finger flange having a rectangular shape configuration.
Figure 12:
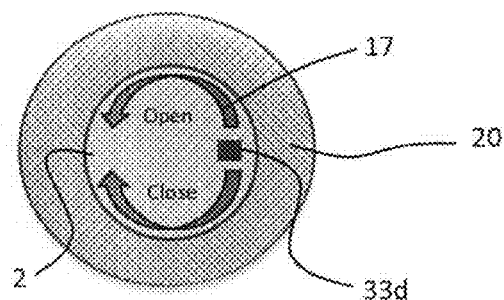
FIG. 12 is a top view of the plunger rod cap and an alternate embodiment of the proximal syringe barrel finger flange having a circular shape configuration.

FIGS. 10-12 illustrate by way of example various configurations/designs of the finger flanges. FIG. 10 illustrates a finger flange 18 having a "wings" configuration, FIG. 11 illustrates a finger flange 19 having a rectangular configuration, and FIG. 12 illustrates a finger flange 20 having a circular configuration. Other shapes/configurations are also contemplated. The designs/shapes may be of varying lengths and depths to optimize function and patient comfort and ease of use.

FIGS. 13A-13F, illustrate different configurations of the plunger rod system designated respectively as systems 110a, 110b, 110c, 110d, 110e, 110f (collectively referred to as plunger rod systems 110), which includes the plunger rod top/cap 2, the thin plunger rod 1a, 1b, 1c, 1d, 1e, 1f, 1g, 1h (collectively plunger rod 1), and the rotatable plunger rod door 22a, 22b, 22c, 22d, 22e, 22f, 22g, 22h, 22i, 22j, 22k (collectively door 22) which is at the bottom or distal end of the plunger rod 1. The plunger rod door 22 is like a foot or angled feet with heels together and extends from the plunger rod 1 in an outwardly (radial) fashion with respect to the longitudinal axis of the plunger rod 1. Thus, to aid understanding, the plunger rod 1 would represent the leg, the door 22 represents the entire foot region and the bottom surface of the door forms the foot 21 which will cover the syringe tip hole or align the opening of the foot 21a, 21b, 21c, 21d, 21e, 21f, 21g, 21h, 21i, 21j, 21k (collectively foot 21) with the hole of the rubber syringe tip/stopper.

As can be understood by the various embodiments, the foot 21 can either have an opening which aligns with the opening in the stopper 7 or can have an open area which aligns with the opening in the stopper 7. In these embodiments, a region of the foot forms a solid surface to cover the opening in the stopper 7.

Figure 13A:
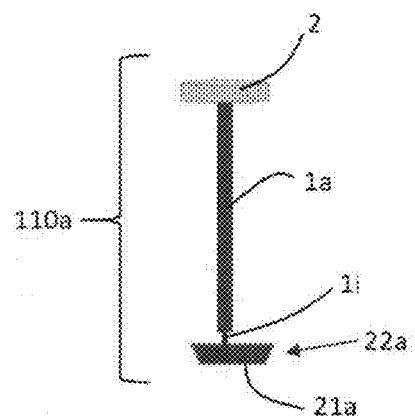
FIGS. 13A, 13B, 13C, 13D, 13E and 13F are side views of alternate embodiments of the plunger rod system of the present invention.
Figure 13B:
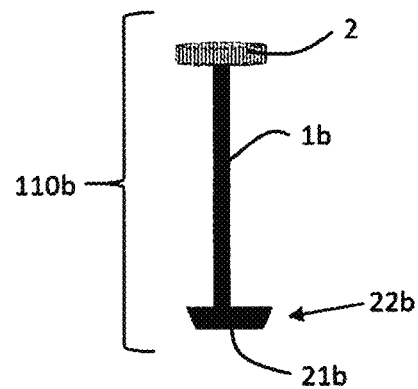
Figure 13C:
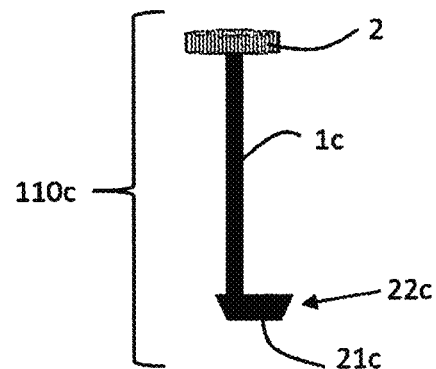
Figure 13D:
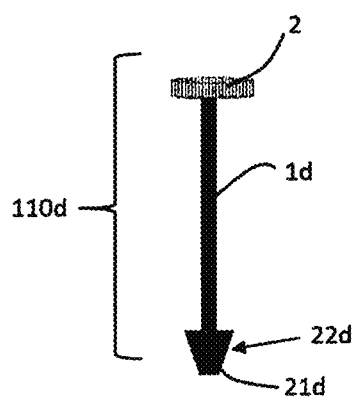
Figure 13E:
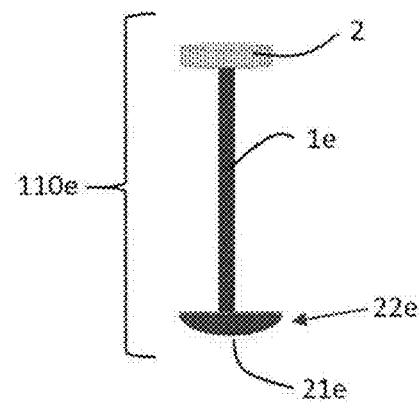
Figure 13F:
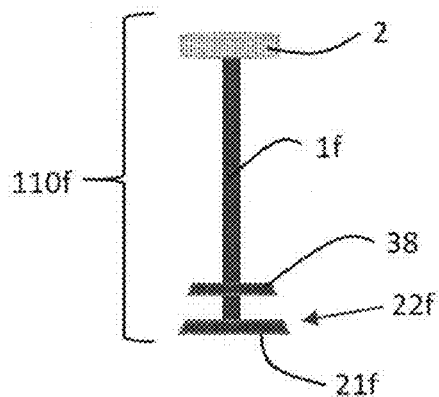

More specifically, in FIG. 13A, the foot 21a of door 22a is spaced slightly from the proximal end of the plunger rod 1a, connected by a thin rod 1i. The foot 21a is shown slightly offset from the longitudinal axis of the plunger rod 1a. In FIG. 13B, the foot 21b and door 22b extends from the distal end of the plunger rod 1b and is also slightly offset from the longitudinal axis. FIG. 13C differs from FIG. 13B in that the foot 21c and door 22c is further offset from the longitudinal axis of plunger rod 1c. In FIG. 13D, door 22d extending from plunger rod 1d is conical while door 22e of FIG. 13E is cup or disc shaped. The cap is the same in these embodiments so has been labeled with reference numeral 2 in FIGS. 13A-13C. These shapes and orientations (e.g., offset) of the door and foot are shown by way of example since other shapes and orientations of the door/foot are also contemplated. In FIG. 13F, the foot 21f of door 22f is centered with respect to the longitudinal axis of the plunger rod 1f.

FIGS. 14A-14E illustrate different configurations of the foot 21, including the open area of the foot 21 of the plunger rod systems which exposes the opening in the stopper 7. The term "open area" as used herein encompasses a space or gap in the door to align with the opening in the stopper 7 or an opening spaced from the perimeter of the door to align with the opening in the stopper 7.

Figure 14A:
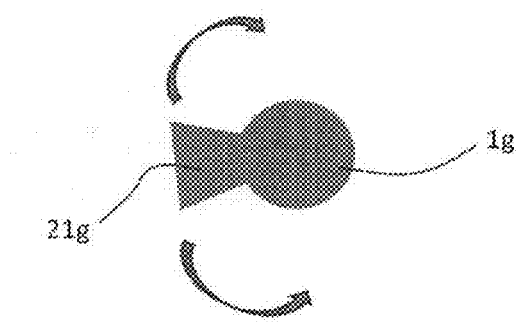
FIGS. 14A 14B, 14C, 14D and 14E, are bottom views of alternate embodiments of the foot of the plunger rod door of the plunger rod systems of the present invention.
Figure 14B:
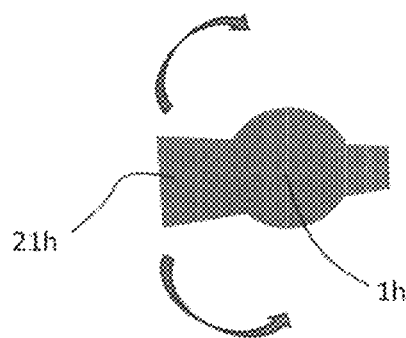
Figure 14C:
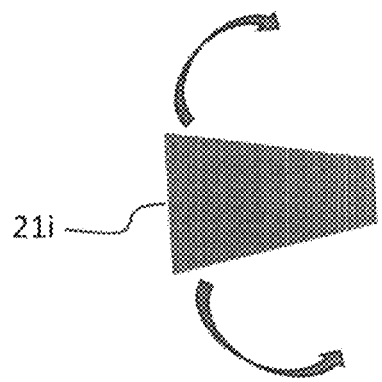
Figure 14D:
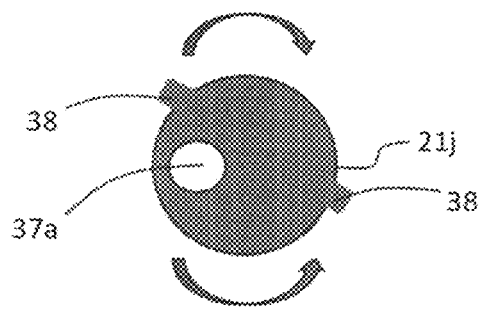
Figure 14E:
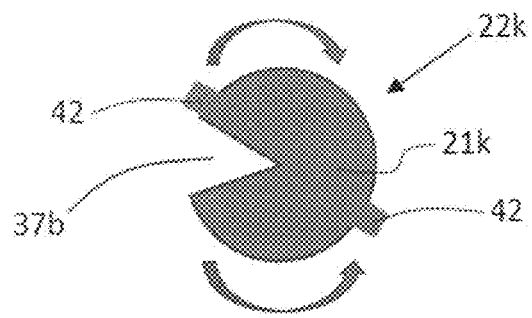

In FIGS. 14A and 14B, foot 21g and 21h of plunger rod 1g and 1h, respectively, have a somewhat triangular or trapezoidal shape. In FIG. 14C, foot 21i has a trapezoidal or conical shape. In FIGS. 14D and 14E, foot 21*j* and 21*k*, respectively, have a circular shape. It should be understood that other shapes/configurations of the foot and/or open area can be utilized to cover or open the hole and attach to the rubber syringe tip/stopper. The open area of the door/foot can also vary as shown for example in FIG. 14D wherein the open area is in the form of a circular opening 37*a* spaced from the periphery and the open area in FIG. 14E is in the form of a gap 37*b* (or removed section or space) that is triangular and extends from the periphery.

The size or coverage of the door and foot of the plunger rod can have a variety of size configurations. For example the size and shape of the door and foot can be enough to cover or seal the hole of the rubber syringe tip/stopper, or it can be larger to provide more coverage and sealing capabilities with the opening or hole of the door being large enough to align with the syringe tip/stopper so the hole is always closed, until the door is opened, rather than the door always being opened until it is closed.

The different Figures show various positioning options for the door and foot as well as a different thinness for the base of the plunger rod. The plunger rod is attached to the plunger rod door in a way that optimizes functionality for rotation (or other movement in alternate embodiments for maneuvering the door) to optimize performance for opening and closing the syringe tip hole 25 and also for attaching proximally to the rubber syringe tip 7.

The plunger rod systems of the present invention in preferred embodiments are not removable from the syringe barrel 5 since the syringe barrel 5 of the present invention has a proximal seal to ensure that insulin does not leak and the syringe can be prefilled and carried for daily use or shipped with a depressed plunger. Additionally, the plunger rod systems of the present invention in preferred embodiments provide a reusable insulin syringe design whereby the syringe is used for a longer term extended basis and the needles are replaced as required. This enables the reusable insulin syringe to be smaller, less expensive and easier to use and carry.

As described above, when the plunger rod top/cap 2 is rotated within the body 35 of the syringe tip/stopper body 7 as selected by the user, the door and foot 21 of the plunger rod 1 is rotated—e.g., to the left to open or to the right to close, to set the foot 21 to either cover and close (seal) the hole in the stopper body 7 or to uncover and open the hole in the stopper body 7. The plunger rod 1 connects the plunger rod top/cap 2 with the plunger rod door 22. As explained previously, the thin plunger rod 1 is strong enough to provide drawing and injection capabilities, while being thin enough to provide space to store insulin and other medications in the syringe barrel.

Figure 15:
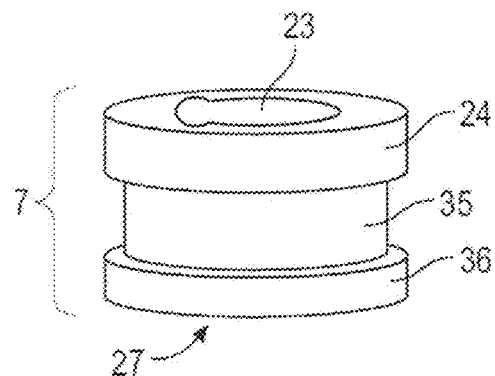
FIG. 15 is a perspective view of the rubber syringe tip/stopper of the syringe assembly of FIG. 1.
Figure 16:
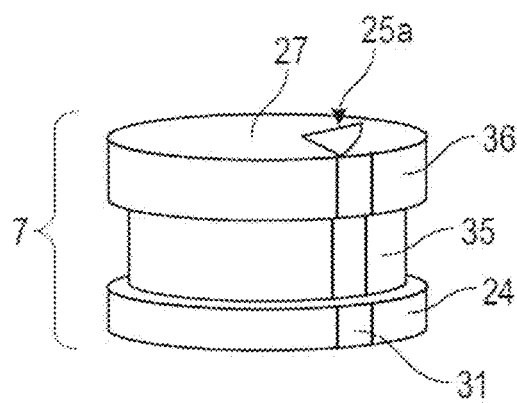
FIG. 16 is an inverted perspective view of the rubber syringe tip/stopper of FIG. 15.
Figure 17:
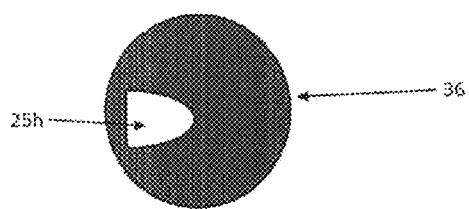
FIG. 17 is a bottom view of an embodiment of the rubber syringe tip/stopper having a semi-circle shaped hole.
Figure 18:
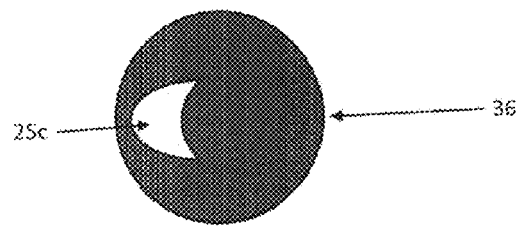
FIG. 18 is a bottom view of an alternate embodiment of the rubber syringe tip/stopper having a moon shaped hole.
Figure 19:
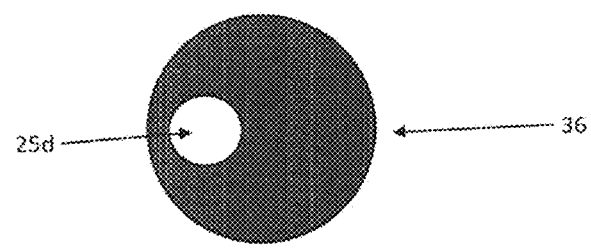
FIG. 19 is a bottom view of an alternate embodiment of the rubber syringe tip/stopper having a round or circular shaped hole.
Figure 20:
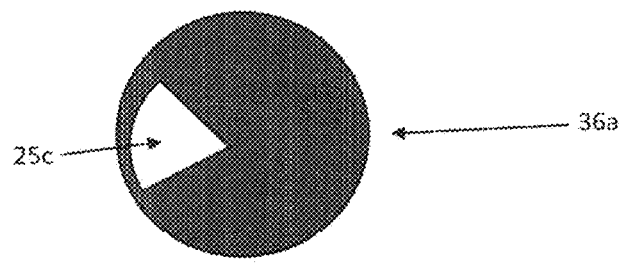
FIG. 20 is a bottom view of an alternate embodiment of the rubber syringe tip/stopper having a triangular or pie shaped hole.

FIGS. 15-21 illustrate various embodiments of the rubber syringe tip/stopper 7 (also referred to herein as the stopper) which is within the enclosed syringe barrel 5 to provide a proximal seal and separate the barrel 5 into the proximal and distal sections. Turning initially to FIG. 15, the sections of the rubber syringe tip/stopper 7 include the rubber syringe tip/stopper bottom overlay 24 for attaching to the plunger rod foot/door 22, the proximal syringe tip/stopper opening 23, the syringe tip body 35 that enables the plunger rod door to rotate freely within the syringe tip/stopper body 35, and the rubber syringe tip/stopper bottom 36 with a hole therethrough. Holes of various sizes and configurations (e.g., holes 25*a*-25*f*) in the bottom 36 of stopper 7 are shown and described below. The syringe tip body 35 is dimensioned larger than the dimension (width) of the foot to enable rotation within the body 35. That is, since the door and foot need to rotate within the stopper 7, the body 35 has an internal region to accommodate such relative movement.

During assembly, to attach the syringe tip/stopper 7 to the rotatable plunger rod 1, the door of the plunger rod is inserted into the hole (opening) 23 at the proximal end of the syringe tip/stopper overlay 24 and is forced fully into the body of the rubber syringe tip/stopper body 35 such that the door 21 of the plunger rod 1 is inside the rubber syringe tip. Thus, the opening 23 is preferably dimensioned similar to the shape of the door or has a shape otherwise configured to enable insertion of the door through the opening 23 and into the body 35 for rotation therein. Note the region of the stopper 7 around the opening can be of material flexible during insertion of the door so that the dimensions of the opening do not necessarily have to be larger than or equal to that of the door. The top and bottom of the rubber syringe tip/stopper form a seal respectively around the top and bottom of the plunger rod door 21, while inside the rubber syringe tip the plunger rod door is able to rotate from side to side to be positioned to cover and close the syringe tip hole, and to rotate to move from covering the hole so the hole is open. This extra space to enable rotation of the door is shown for example in FIG. 22*a* wherein space 35*a* is provided in body 35.

The opening 23 is wider than the diameter of the plunger rod and does not fully cover the plunger rod door to provide space for fluid flow through the stopper when the hole is open.

Note since the barrel of the syringe of the present invention is enclosed on both the proximal and distal ends, in preferred embodiments, the user will not be required to attach or detach the rubber syringe tip/stopper since the user will not have access to it and it will normally come attached.

The plunger rod can include a stopper base such as illustrated in the embodiment of FIG. 13F. The stopper base 38 is supported on plunger rod 1*f* and is used as a base for the rubber syringe tip/stopper to sit on. Note a stopper base can be used with the other embodiments disclosed herein.

The syringe tip/stopper body 35 can have a variety of heights/lengths (from proximal to distal) based on the thickness of the door and foot and also in the embodiments using a stopper base, based on the distance between the foot and the stopper base.

The proximal opening 23 of the rubber syringe tip/stopper 7 not only facilitates entry of the plunger rod door into the syringe tip/stopper 7, but also ensures the rubber syringe tip/stopper 7 does not seal the plunger rod completely so there is space for insulin and other medications to move freely through the rubber syringe tip/stopper 7 when the plunger rod door is set to the open position and the hole of the syringe tip/stopper is not covered. This enables the plunger rod system and rubber syringe tip/stopper 7 to move freely through a prefilled syringe.

The rubber syringe tip/stopper 7 can include a marking 31 on the body 35 (FIGS. 3, 16 and 27) to indicate to the user where the hole of the rubber syringe tip/stopper 7 is located to assist with aligning the foot or the opening of the plunger rod door with the syringe tip/stopper marking or hole to visibly confirm the hole or marking 33 of the cap 2 is aligned with the rubber syringe tip/stopper marking 31. When these markings are aligned, the hole would be opened or in alternate embodiments, be closed, depending on the configuration used.

Figure 21:
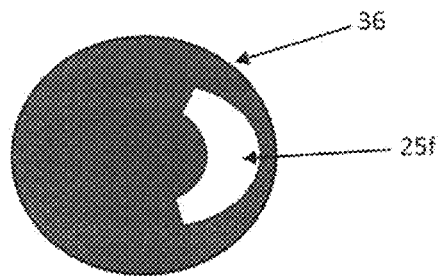
FIG. 21 is a bottom view of an alternate embodiment of the rubber syringe tip/stopper having a crescent shaped hole.
Figure 22:
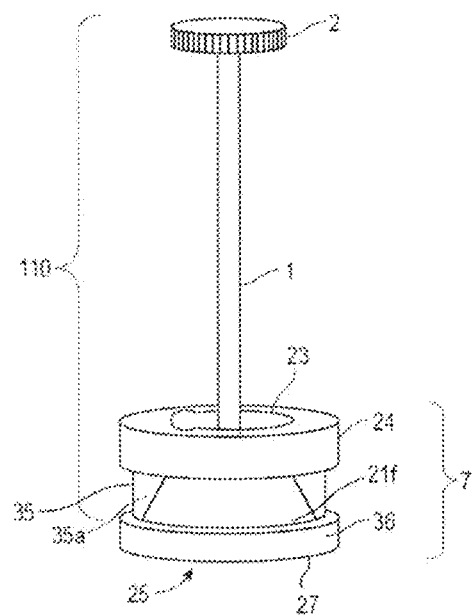
FIG. 22 is a side view of one embodiment of the plunger rod system shown attached to an embodiment of the stopper.

The hole (opening) at the bottom in the rubber syringe tip/stopper can take a variety of different shapes and includes for example shapes represented in FIGS. 16-21 which show a triangular pie shape hole 25*a* (FIG. 16) on the bottom surface 27, semi-circle shaped hole 25*b* (FIG. 17), moon shaped hole 25*c* (FIG. 18), circular shaped hole 25*d* (FIG. 19), pie shaped hole 25*e* (FIG. 20) and crescent shaped hole 25*f* (FIG. 21). Other size holes and shapes are also contemplated. Thus, the rubber syringe tip/stopper hole can have a variety of size and shape configurations, and the size of the hole may be a variety of sizes with the optimal size being such that the hole is large enough to quickly allow medication e.g., insulin, to flow through the opening so the syringe tip/stopper and plunger rod moves through the medication rapidly, but small enough to optimize the sealing capabilities of the syringe tip/stopper for syringe filling and injection performance.

To cover the hole (e.g., holes 25*a*-25*f*), in the syringe tip 7, the foot or bottom 21 of the plunger rod door 22 (such as those of FIGS. 13A-14E) is positioned directly over the syringe tip hole (such as those of FIGS. 16-21). As noted above, the foot 21 of the plunger rod door 22 is the part of the door 22 that provides coverage and closure to the hole. The foot configuration can conform to the hole configuration, or be larger than the hole, or otherwise configured and/or sized to accommodate the hole, so that the foot would cover the hole for sealing and be sufficiently removed from hole coverage for opening.

In use, to open the hole, the plunger rod door 1 is rotated so the hole (e.g., hole 25*a*, 25*b*, 25*c*, 25*d*, 25*e*, 250 of the rubber syringe tip 7 is aligned with the open area (e.g., area 37*a* or 37*b* of FIGS. 14D and 14E) of the plunger rod door 22 so the open area is not covered or sealed by the foot of the plunger rod door and is open to allow insulin or other medications to flow through the rubber syringe tip/stopper and the door so the syringe tip can be repositioned.

To facilitate rotation of the door of the plunger rod, the rubber syringe tip/stopper preferably remains stable and does not rotate (or has limited rotations) in any side to side direction within the syringe barrel, thereby enabling the plunger rod door to move and rotate relative to the rubber syringe tip and freely within/inside the rubber syringe tip and to make coverage of the rubber tip/stopper hole or alignment of the open area of the door with the hole easy to complete. However, the rubber syringe tip/stopper moves axially along with the plunger rod. That is, axial movement of the plunger rod changes the axial position of the syringe tip/stopper within the barrel of the syringe for dosage adjustment.

The shape of the foot of the plunger rod door is such that when the foot of the plunger rod door is over (or, in alternate embodiments, below) the hole of the syringe tip/stopper, the hole will be completely covered and tightly sealed such that the syringe tip/stopper hole is closed, and the syringe is able to draw in or inject the insulin or other medication. Conversely, when the hole or open area of the plunger rod door or foot is not over (or below in alternate embodiments) the hole of the rubber tip/stopper, the syringe tip/stopper will be open and the plunger rod system will be able to move within a syringe filled with insulin or other medications.

The plunger rod door is shaped so that the rubber syringe tip/stopper is able to attach to the plunger rod, and the bottom or distal end of the plunger rod is flat or rounded slightly to ensure a tight fit with the stopper and acts like a "foot" to be able to completely "seal" the hole of the rubber syringe tip when moved to the "closed" position to draw insulin or medication into the syringe and to inject.

FIG. 22A shows the plunger rod door 21*f* of the embodiment of FIG. 13F by way of example attached to the rubber syringe tip/stopper 7 (of the embodiment of FIG. 15) and shows the top of the syringe tip/stopper 24 that forms the attachment or seal for the plunger rod door to ensure the two components of the syringe system are attached and connected. Region 35 of stopper 7 is shown transparent for illustrative purposes to show the door 21*f* within the stopper 7 and the space 35*a* for rotation.

In some embodiments, barriers or "bumpers" can be provided on the bottom or on the inner sides of the syringe tip/stopper to restrict the rotation of the plunger rod door when the cap/plunger rod are rotated. The raised bumpers can also provide a tactile feel to the user to indicate complete rotation to open or close the opening of the stopper. Several embodiments of such barriers or stopper are shown in FIGS. 23A-24C. The barriers extend proximally from a proximal surface of the bottom region 36 of the stopper 7 forming raised walls that stop the plunger rod "door" from further rotation within the rubber syringe tip/stopper when the plunger rod is rotated in either direction to position the plunger rod door in an open or closed position. In alternate embodiments where the foot is below the opening, the barriers would extend distally from the distalmost (lowermost) surface of the stopper 7.

In some embodiments, the plunger rod can also rotate the syringe tip/stopper if it is further rotated after contacting the bumps. However, at this point, the door of the plunger rod and the stopper 7 will rotate together so the position of the door with respect to the opening in the stopper is not effected. That is, is such embodiments, with the use of these barriers, both the plunger rod door and the rubber syringe tip/stopper will rotate together as the plunger rod door will be rotating the stable rubber syringe tip/stopper once the barrier or "bumpers" are engaged by the plunger rod door. The various barriers can be used with any of the embodiments of the syringe tip stopper and any of the embodiments of the door/foot and/or openings. Note barriers of other shapes, as well as of a different number than shown, can be utilized to provide a stop to the clockwise and counterclockwise rotation of the door of the plunger rod.

Figure 23A:
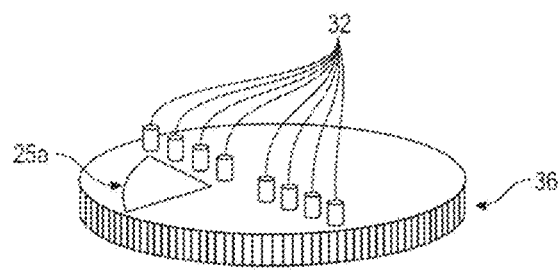
FIG. 23A is a perspective view of the inner portion of the rubber syringe tip/stopper of an alternate embodiment of the present invention having raised barriers to limit rotation of the plunger rod in either direction.
Figure 23B:
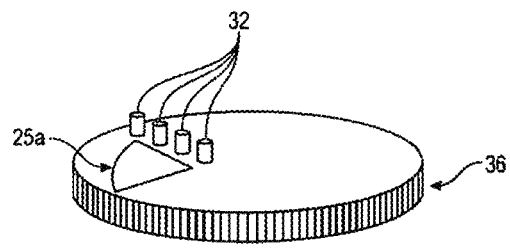
FIG. 23B is a perspective view of the inner portion of the rubber syringe tip/stopper of an alternate embodiment having raised barriers to limit rotation of the plunger rod in either direction.

FIGS. 23A and 23B show raised spaced apart barriers which are in the form of individual raised rods 32 that are attached to the inside of the syringe tip/stopper 7 and are placed inside and across the bottom 36 of the syringe tip stopper 7, extending proximally from bottom (distal) region 36. Barriers 32 stop the plunger rod door from rotating beyond or past the raised barriers 36 and force the rubber syringe tip/stopper 7 to be rotated or directed by the rotation of the plunger rod engaged by the user. This will ensure that when the plunger rod door is rotated to the left to open the hole of the syringe tip, that the barriers that stop the plunger rod door from rotating too far to the left are in a position that when the plunger rod door is stopped by the barriers, the rubber syringe tip/stopper hole is totally open and the foot of the plunger rod door is not covering the hole and the open area of the plunger rod door is aligned with the syringe tip/stopper hole. Further, there are barriers placed to the right of the syringe tip hole, so that when the plunger rod door is rotated to the right to cover or close the syringe tip/stopper hole, the plunger rod door is stopped in a position such that the foot of the plunger rod door covers the syringe tip hole and the hole is closed or covered. The design or location of the barriers will be determined by the location of the syringe tip/stopper hole and the design of the plunger rod door and foot.

Figure 24A:
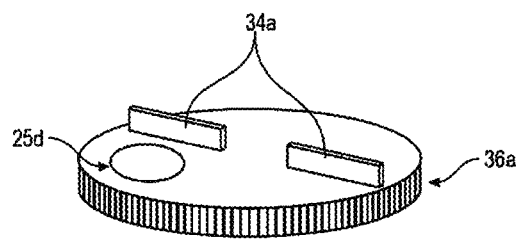
FIG. 24A is a perspective view of the inner portion of the rubber syringe tip/stopper of an alternate embodiment having raised barriers to limit rotation of the plunger rod in either direction.
Figure 24B:
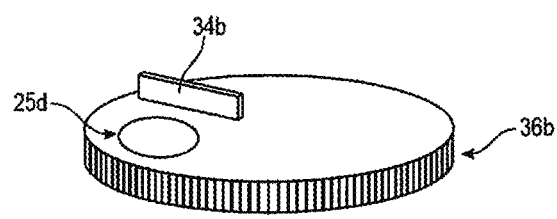
FIG. 24B is a perspective view of the inner portion of the rubber syringe tip/stopper of an alternate embodiment having raised barriers to limit rotation of the plunger rod in either direction.
Figure 24C:
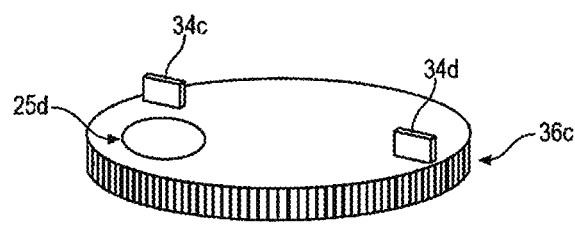
FIG. 24C is a perspective view of the inner portion of the rubber syringe tip/stopper of an alternate embodiment having raised barriers to limit rotation of the plunger rod in either direction.

An alternate system for stopping or restricting the rotation of the plunger rod door is illustrated in FIGS. 24A-24C. Rather than using raised barriers, this system uses raised walls or side walls or "bumpers" 34*a*, 34*b*, 34*c*, 34*d* (collectively bumpers 33) that are elongated raised barriers extending proximally from bottom region 36a 36b, 36c, respectively (collectively bottom region 36). In alternate embodiments, they extend distally. Barriers or bumpers 34a cover most of the radius of the syringe tip/stopper or are positioned on the inner side of the syringe tip/stopper at the appropriate positions such that when the plunger rod is rotated to the left, the raised wall stops the motion of the plunger rod door so the plunger rod foot of the plunger rod door is not covering the syringe tip hole and the hole is open. Further, the raised walls of the inside of the syringe tip will also be positioned so when the plunger rod door is rotated to the right, the foot of the plunger rod door is positioned above the syringe tip hole and the hole is covered/sealed or closed. The design or location of the barriers will be determined by the location of the syringe tip/stopper hole and the design of the plunger rod door and foot.

In the embodiment of FIGS. 24A and 24C, the two walls or bumpers are on opposite sides of bottom region 36a, 36c, respectively, extend upwardly therefrom. In FIG. 24B, one wall 34b is provided. When the walls 34 are placed along the side of the rubber tip/stopper body, the plunger rod door would have a side area or "wing" 42 (FIGS. 14D and 14E) that would be stopped by the barrier or "bumper" during rotation. When the barrier catches the side area or "wing" during rotation, the plunger rod and rubber tip/stopper would rotate together until the direction was changed. The design or location of the barriers along the body will be determined by the design of the plunger rod door with side area or "wings".

Note that other forms of barriers to limit rotation are also contemplated. Additionally, other types of stops or features could be provided to restrict rotation or maneuvering of the door. It should be appreciated that in some embodiments, barriers are not provided.

Figure 24D:
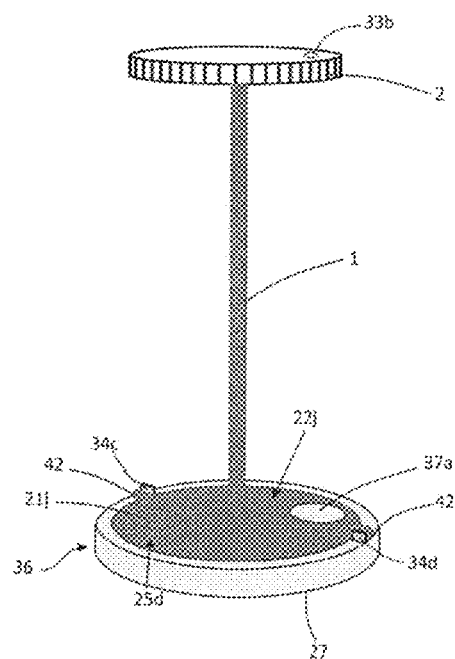
FIG. 24D is a perspective view of the plunger rod system with the foot of FIG. 14D covering the hole of the stopper with raised barriers to limit rotation of the plunger rod in either direction.
Figure 24E:
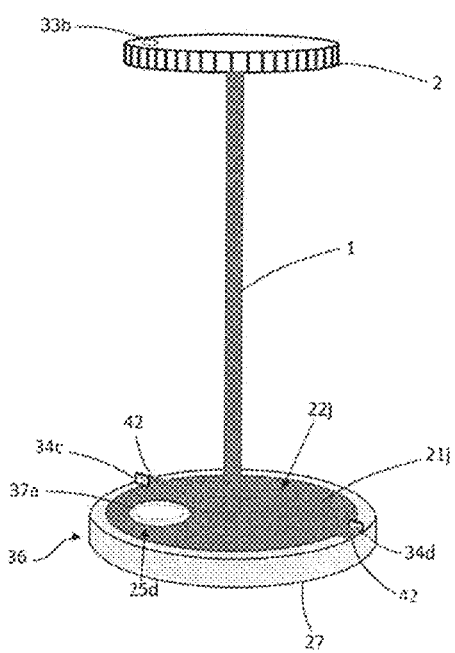
FIG. 24E is a perspective view similar to FIG. 24D showing the foot of the plunger rod system aligning the hole of the foot with the hole of the stopper with raised barriers to limit rotation of the plunger rod in either direction.

FIGS. 24D and 24E show the plunger rod system covering and opening the hole of the stopper. These Figures show the opening and closing of the foot 24j of the embodiment of FIG. 14D by way of example, however, it should be appreciated that the other foot embodiments (and plunger rod systems) as disclosed herein can function in the same manner to cover and open the hole. FIG. 24D shows the foot 21j of plunger rod door 22j covering the hole 25d of the stopper 7—thereby closing the hole. (Note only a portion (bottom portion 35) of the stopper 7 is shown for clarity). Bumpers 34c and 34d restrict the rotation of the foot 24j of the plunger rod 1 by blocking the rotation of "wings" 42 within the stopper—ensuring the stopper 7 is in a "closed" position and the stopper hole 25d is covered. FIG. 24E shows the hole 25d of the stopper 7 open and aligned with opening 37a of plunger rod door 22j, thus enabling fluid to flow through the stopper.

With the system of the present invention, a user will be able to fill their insulin syringe (or syringe containing other medication) and then be able to depress the plunger rod to close the syringe tip and then carry the prefilled insulin syringe (with the plunger depressed) to use throughout the day (multiple injections) or for a single injection if desired. This provides a compact configuration for storage reducing the overall dimensions (length) since the pre-filled syringe has the plunger in a depressed (distal) position so its projection from the barrel is minimized.

In certain embodiments the user will also be able to fill the syringe of the present invention using a second syringe to inject the insulin or other medication directly into the syringe without engaging the plunger rod system and with the plunger rod in a depressed position.

Additionally, with insulin or other medications, manufacturers will be able to prefill the syringe and then depress and close the plunger so the prefilled syringe is then easier and more convenient to ship and store in a prefilled state as it will have a reduced dimension (length).

The syringe assembly of the present invention allows for the overall length and width of a pre-filled syringe to be minimized for packaging, shipping and storage savings and to reduce storage space in hospitals, medical clinics and patient homes or other locations where prefilled syringes are used.

The syringes of the present invention also enable in some embodiments, mixing of two substances, e.g., two medications or one medication and another substance, e.g., powder or fluid. More specifically, manufacturers will be able to prefill the syringe with two different drugs or drug formulations, such as two liquid medications, with one drug residing in the distal portion (section) of the syringe barrel and in front of (distal of) the closed rubber syringe tip/stopper and the other drug residing in the proximal portion (section) proximal (behind) the closed rubber syringe tip/stopper. The drug in the distal section of the barrel can be a fluid or powder for example. In this prefilled state, the plunger rod system would not be fully depressed due to the drug that is prefilled and stored distally and in front of the closed rubber syringe tip/stopper. That is, the plunger rod needs to be in a more proximal position so the stopper is in a more proximal position to provide sufficient space in the distal section for one of the medications. However, the plunger rod is not fully retracted because the stopper needs to be in a sufficient distal position to allow space proximal of the stopper for the other medication. The extent of retraction of the plunger rod is dependent on the amount of medication in the distal section of the barrel.

Figure 27:
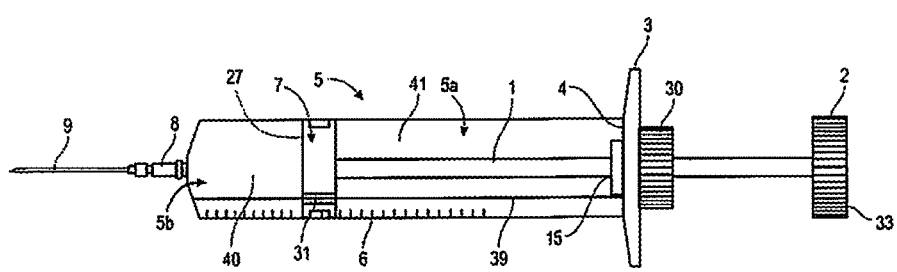
FIG. 27 is a perspective view of the syringe assembly in accordance with an embodiment of the present invention wherein the syringe is prefilled or filled with two different medications that are separated by the closed/sealed rubber syringe tip/stopper that is not in a fully depressed position.

FIG. 27 illustrates one example of the syringe prefilled with two different drugs with one drug 40 within the syringe barrel distal to the closed rubber syringe tip/stopper 7 (in distal section 5b) and another drug 41 proximal to the closed rubber syringe tip/stopper (in proximal section 5a). The syringe shown is the syringe of FIG. 3 but other syringes disclosed herein can also be utilized to store and mix two different fluids/medication. In this embodiment, convenience for the user is increased and the mixing of the two drugs will be faster and improved as the user can open the syringe tip-stopper by rotation of the plunger rod and door to allow the two drugs to mix as the drug from the proximal section flows through the aligned openings in the door/foot and stopper to mix with the drug in the distal section. That is, with the plunger rod and the rubber syringe tip/stopper in the open position, the two drugs can be mixed before the drugs are injected. Thus, with this system, users will more easily be able to fill and mix two different drugs in a single syringe because of the opening and closing mechanism of the rubber syringe tip/stopper and also due to the closed proximal section that can enable medication to be injected directly into the proximal portion of the syringe. It is also contemplated that the distal section of the barrel can be filled by injection though a distal end of the syringe or by removal of the plunger rod and stopper. Thus, when the closed plunger rod door is sealing the rubber syringe tip/stopper, the syringe barrel can be prefilled with two different medications with the plunger rod extended and not fully depressed, thereby enabling a single-barrel syringe to function like a dual-chamber syringe.

The syringe can also be prefilled with a drug in a dry or powder state (particle drug formulation) that is then mixed and turned into a liquid medication with the second liquid drug or inert liquid solution when the rubber syringe tip/stopper is opened and drug in the dry or powder state is then mixed with the liquid solution to then form a prefilled mixed liquid drug solution.

Figure 25A:
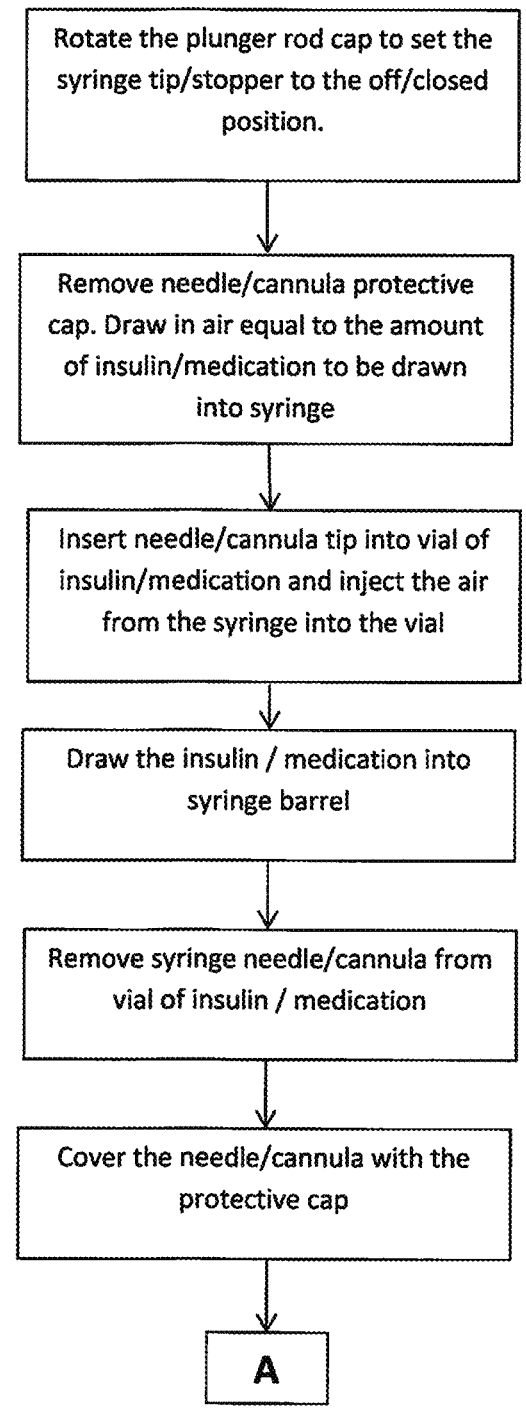
FIGS. 25A and 25B provide a flow chart showing the steps to fill the syringe to then carry/store/ship the syringe with syringe plunger in a depressed position in accordance with an embodiment of the present invention.
Figure 25B:
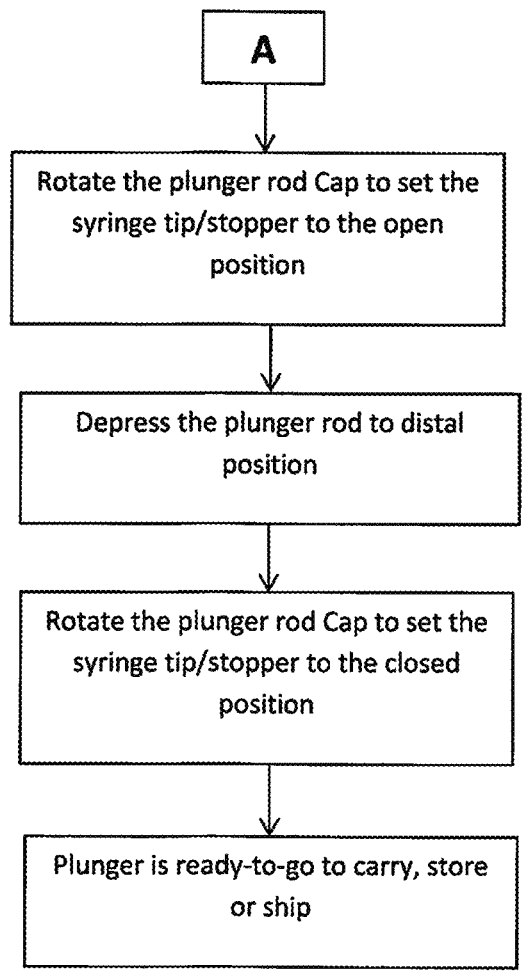

Turning now to use of the syringe and to the embodiments of FIGS. 1-26, the steps required to prefill the syringe to then carry/store/ship the syringe in the depressed position are set forth below. The plunger rod is then depressed to save space and make the injection step safer and more convenient for the user. The steps to fill the syringe and set the plunger rod into the depressed position are outlined in the flow chart of FIGS. 25A-25B and include the following steps:

1. Rotate the plunger rod cap to set the syringe tip/stopper to the Off/Closed position.
2. Remove needle/cannula protective cap. Draw in air equal to the amount of insulin/medication to be drawn into syringe.
3. Insert needle/cannula tip into vial of insulin/medication and inject the air from the syringe into the vial
4. With the syringe tip/stopper in the Off/Closed position, draw the desired amount of insulin/medication into syringe barrel
5. Remove syringe needle/cannula from vial of insulin/medication
6. Cover the needle/cannula with the protective cap
7. Rotate the plunger rod cap to set the syringe tip/stopper to the open position. (Note steps 6 and 7 can be done in reverse order but it is preferred to cap the needle/cannula as soon as possible)
8. Depress the plunger rod to distal position
9. Rotate the plunger rod cap to set the syringe tip/stopper to the closed position to ensure insulin/medication does not leak
10. Plunger is ready-to-go to carry, store or ship To use and inject insulin or other medication with the syringe filled, the user would then undertake fewer steps compared with using a traditional insulin syringe requiring the insulin or other medication to be drawn for each injection.

Figure 26A:
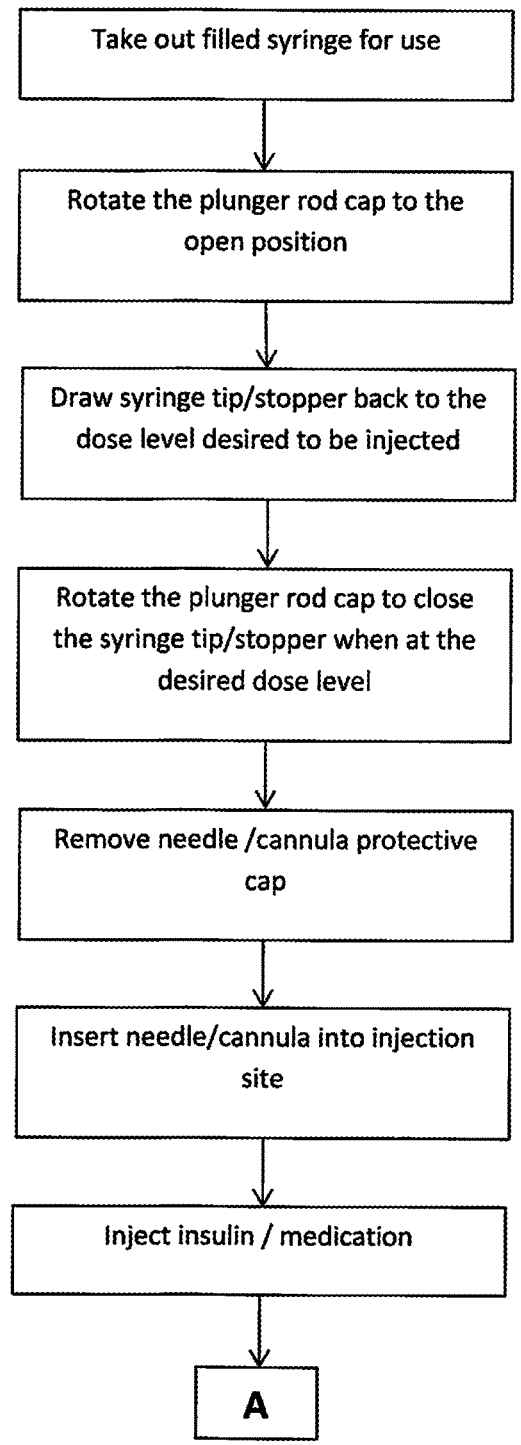
FIGS. 26A and 26B provide a flow chart showing the injection steps for the syringe to inject insulin or other medications using the filled syringe with the plunger rod initially in the depressed position in accordance with an embodiment of the present invention.
Figure 26B:
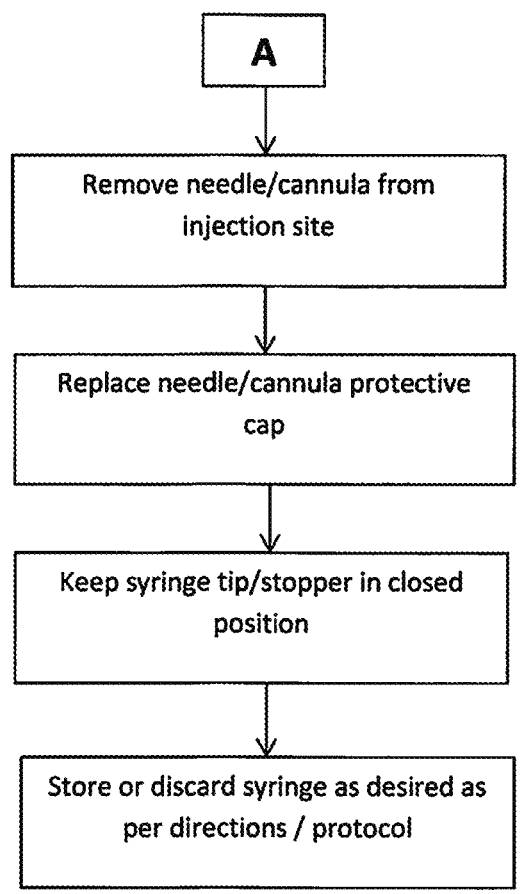

With the system of the present invention the user will be able to inject insulin or other medications using the following steps outlined in the flow chart of FIGS. 26A-26B:

1. Take out filled syringe for use
2. Rotate the plunger rod cap to the open position to align the holes and to move the foot of the plunger rod door away from the rubber syringe tip/stopper hole to open the syringe tip/stopper
3. With rubber syringe tip/stopper set in the open position and the syringe barrel pointed down to ensure insulin/medication is at the distal end of the syringe, draw syringe tip/stopper back to the dose level desired to be injected
4. Rotate the plunger rod cap to close the syringe tip/stopper when at the desired dose level
5. Remove needle/cannula protective cap
6. Insert needle/cannula into clean/prepared injection site
7. Inject insulin/medication (like a traditional syringe)
8. Remove needle/cannula from injection site
9. Replace needle/cannula protective cap
10. Keep syringe tip/stopper in "closed" position
11. Store or discard syringe as desired as per directions/protocol These steps can be repeated for each injection of a series of injections possible with the syringe of the present invention.

With the system of the present invention, the risk of needle stick injuries will be reduced since the needle is exposed for significantly less time.

Also, with the system of the present invention the user can keep the syringe tip/stopper in the closed position and use the syringe like standard syringe.

The syringe assembly enables steps for injection to be used that may reduce the total number of steps needed to inject insulin or medication when the syringe is filled for use.

In some embodiments, the syringe assembly can have a housing for a hypodermic needle or cannula, but does not come with the hypodermic needle or cannula attached and the needle housing is designed to be used with a replacement needle to be attached by the user prior to use and injections. The attached hypodermic needle or cannula has a variety of gauges and lengths that can be used based upon clinical or patient requirements.

In some embodiments, the syringe assembly includes a non-needle design option where the syringe comes without a needle hub or having the needle attached, and other distal ejection port assemblies are used.

The syringes disclosed herein can be used during interventional, surgical, and other general healthcare use and procedures requiring syringes and prefilled syringes.

Figure 28A:
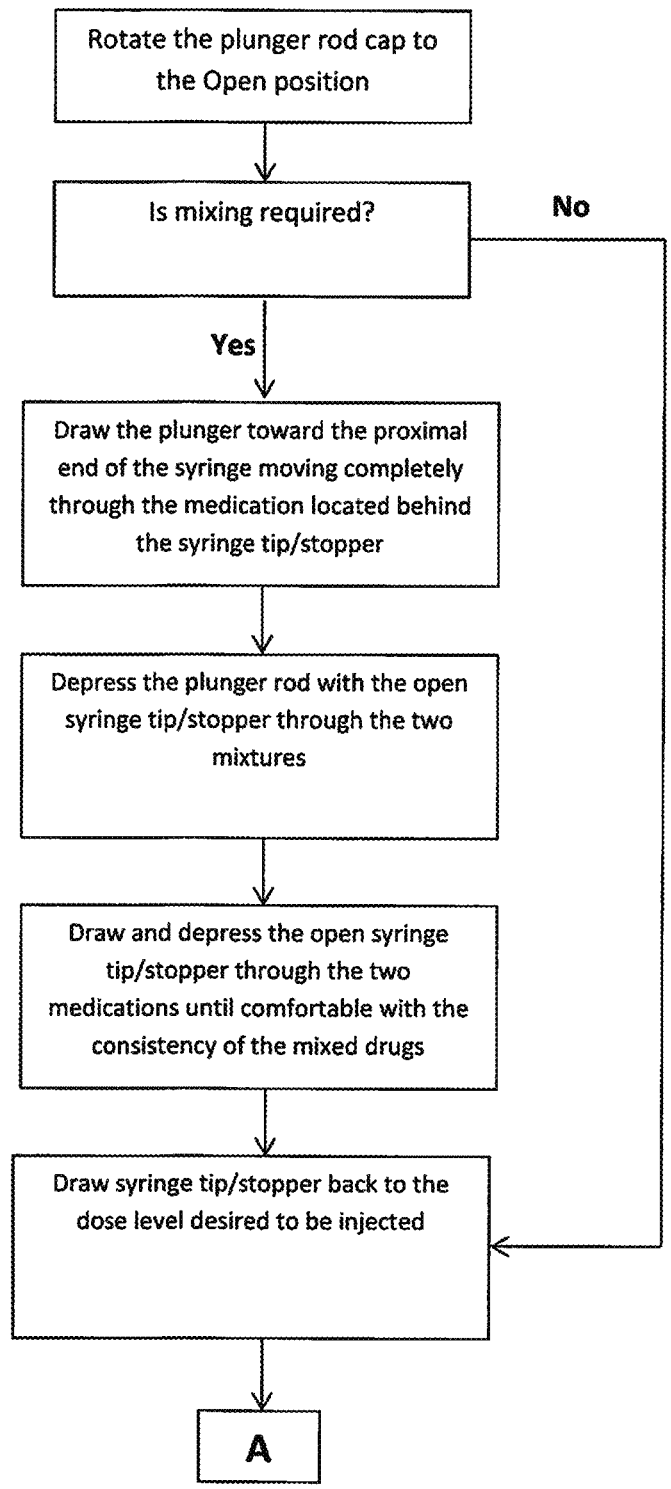
FIGS. 28A and 28B provide a flow chart illustrating steps for mixing and injecting two medications in accordance with an embodiment of the present invention.
Figure 28B:
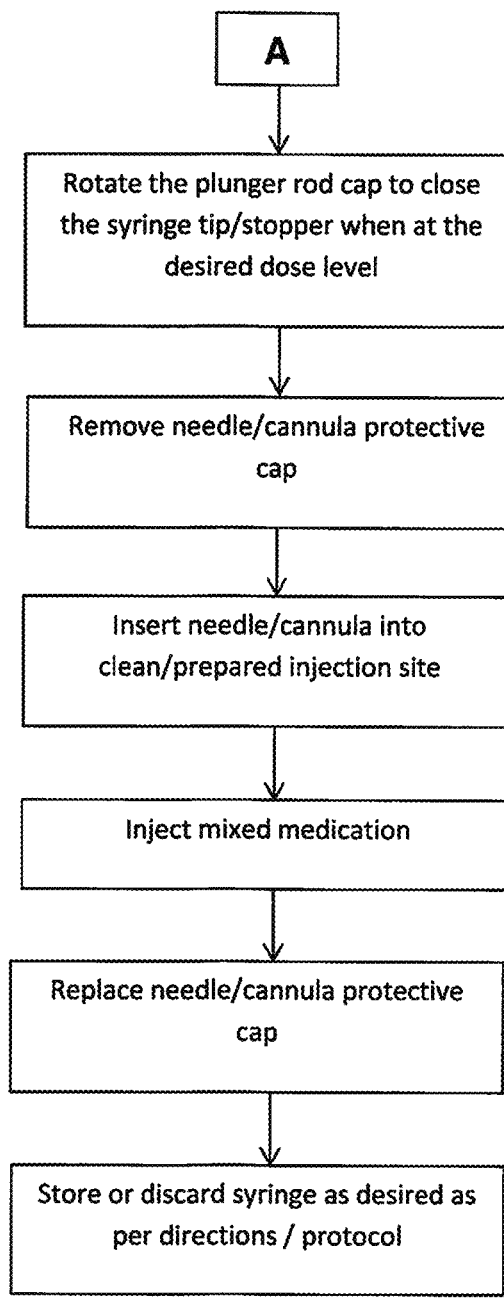

FIGS. 28A-28B provide a flow chart depicting an alternate embodiment for injecting and mixing two medications prefilled within the syringe to enable shipping, storage and use for a prefilled syringe filled with two drugs. The steps are as follows:

1. Rotate the plunger rod cap to the open position to align the holes and to move the foot of the plunger rod door away from the rubber syringe tip/stopper hole to open the syringe tip/stopper. If mixing of the medications is not required proceed to step 5.
2. With the syringe tip/stopper in the open position, draw the plunger towards the proximal end of the syringe moving completely through the medication located behind the syringe tip/stopper.
3. Depress the plunger rod with the open syringe tip/stopper through the two mixtures.
4. With the syringe tip/stopper still in the open position, draw and depress the open syringe tip/stopper through the two medications until user is comfortable with the consistency of the mixed drugs. With the syringe in the proximal most position the user may also shake the contents of the syringe.
5. With a satisfactory mixture and with rubber syringe tip/stopper set in the open position and the syringe barrel pointed down to ensure the mixed medication is at the distal end of the syringe, draw syringe tip/stopper back to the dose level desired to be injected.
6. Rotate the plunger rod cap to close the syringe tip/stopper when at the desired dose level.
7. Remove needle/cannula protective cap.
8. Insert needle/cannula into clean/prepared injection site.
9. Inject mixed medication.
10. Remove needle/cannula from injection site.
11. Replace needle/cannula protective cap.
12. Store or discard syringe as desired as per directions/protocol.

For purposes of the descriptions here, it is to be understood that the embodiments described may assume alternative variations and embodiments. It is also to be understood that the specific devices illustrated in the accompanying drawing figures and described herein are exemplary and should not be considered as limiting. Various modifications, additions and alternative designs will become apparent to those skilled in the art in light of the foregoing teachings without departing from the scope of the invention. Additionally, the scope of the invention is indicated by the following claims rather than solely by the foregoing description. All changes and variations that fall within the meaning and range of equivalency of the claims are to be embraced within their scope.

What is claimed is:

1. A syringe assembly comprising:
   a) a barrel for storing a medication, the barrel having a proximal section and a distal section;
   b) a stopper positioned within the barrel and having a first opening, the stopper separating the proximal and distal sections of the barrel, the stopper having a second opening having a first transverse dimension,
   c) a plunger movable axially within the barrel, the plunger having a plunger rod extending through the second opening, the plunger rod having a second transverse dimension less than the first transverse dimension of the second opening to provide a gap for the medication to flow through the second opening around the plunger rod proximally of the stopper; and
   d) a cover extending radially from the plunger, the cover movable within the barrel from an open position to a closed position, wherein in the open position the cover exposes the first opening in the stopper to enable the medication to flow through the gap and within the barrel from the proximal section to the distal section and in the closed position the cover covers the first opening to prevent the flow of medication from the proximal section to the distal section.

2. The syringe assembly of claim 1, wherein the plunger is rotatable to move the cover between the open and closed position.

3. The syringe assembly of claim 1, wherein the stopper is attached to the plunger and moves axially with axial movement of the plunger.

4. The syringe assembly of claim 1, wherein the stopper includes a body portion having a dimension greater than a dimension of the cover so the cover can freely rotate within the body portion of the stopper.

5. The syringe assembly of claim 1, wherein the cover has an open area movable into alignment with the first opening in the stopper to allow the flow of medication.

6. The syringe assembly of claim 1, wherein the cover has an opening therethrough movable into alignment with the first opening in the stopper to allow the flow of medication through the opening in the cover and the first opening in the stopper.

7. The syringe assembly of claim 1, further comprising a first and second set of markings on an outer wall of the barrel to indicate a dose of fluid to be injected from the barrel, the first set of markings containing numerals facing proximally and the second set of markings containing numerals facing distally.

8. The syringe assembly of claim 1, wherein the plunger includes a cap, the cap having an indicator to indicate alignment of an opening area or an opening in the cover with the first opening in the stopper.

9. The syringe assembly of claim 1, wherein the cover is offset from a longitudinal axis of the plunger rod.

10. The syringe assembly of claim 1, further comprising a proximal and distal seal positioned on the plunger rod.

11. The syringe assembly of claim 1, wherein a second medication is positioned in the distal section of the barrel, and the cover is movable to an open position to mix the second medication with the medication from the proximal section.

12. The syringe assembly of claim 1, wherein the plunger is depressable to inject the medication from the barrel and the plunger is stored in a depressed position.

13. The syringe assembly of claim 1, wherein the first opening in the stopper has a transverse dimension less than a transverse dimension of the second opening.

14. The syringe assembly of claim 1, wherein the cover is positioned proximal of the first opening in the stopper.

15. The syringe assembly of claim 1, wherein the second opening is dimensioned to receive the cover therethrough so the cover can be positioned adjacent the first opening in the stopper.

16. The syringe assembly of claim 1, wherein the stopper further comprises at least one bumper to restrict rotation of the cover and to provide an indication when the cover is in the closed position.

17. A syringe assembly comprising:
   a) a barrel for storing a medication, the barrel having a proximal section and a distal section;
   b) a stopper positioned within the barrel and having a first opening in a distal surface for medication flow through the stopper for flow from the distal section to the proximal section of the barrel, the stopper separating the proximal and distal sections of the barrel, the stopper movable axially within the barrel, the first opening selectively closable and openable to allow flow of medication from the proximal section to the distal section to provide a selected dose of medication in the distal section of the barrel; and
   c) a plunger movable axially distally within the barrel to inject the medication which flowed into the distal section of the barrel from the proximal section; and
   d) a cover extending from the plunger, the plunger rotatable to move the cover from a first position covering the first opening in the stopper to a second position spaced from the first opening to enable flow of medication through the first opening, wherein the first opening is a single opening providing the only path for medication flow from the distal section to the proximal section.

18. The syringe assembly of claim 17, wherein the plunger is depressable to inject the medication from the barrel and the plunger is stored in a depressed position.

* * * * *